United States Patent [19]

Massie

[11] 3,931,295

[45] Jan. 6, 1976

[54] HYDROXYLATION OF AROMATIC COMPOUNDS

[75] Inventor: Stephen N. Massie, Palatine, Ill.

[73] Assignee: Universal Oil Products Company, Des Plaines, Ill.

[22] Filed: July 23, 1974

[21] Appl. No.: 491,008

[52] U.S. Cl. .................. 260/502.4 R; 260/502.4 P; 260/502.5; 260/509; 260/510; 260/512 R; 260/512 C; 260/519; 260/520; 260/521 B; 260/523 R; 260/523 A; 260/621 G
[51] Int. Cl.$^2$ ............ C07F 9/38; Co7F 143/64; C07F 143/44; C07C 65/04
[58] Field of Search .. 260/621 G, 502.4 R, 502.4 P, 260/502.5, 509, 510, 512 R, 512 C, 519, 520, 521 B, 523 R, 523 A

[56] References Cited

UNITED STATES PATENTS

| | | | |
|---|---|---|---|
| 2,395,638 | 2/1946 | Milas | 260/621 G |
| 2,437,648 | 3/1948 | Milas | 260/621 G |
| 3,531,519 | 9/1970 | Parkin et al. | 260/621 G |
| 3,580,956 | 5/1971 | Bloch | 260/621 G |

*Primary Examiner*—Joseph E. Evans
*Attorney, Agent, or Firm*—James R. Hoatson, Jr.; Raymond H. Nelson; William H. Page, II

[57] ABSTRACT

Nuclear hydroxylation of aromatic compounds is effected by treating said aromatic compounds with hydrogen peroxide in the presence of a catalyst comprising an alkaline solution containing a salt of hydrocyanic acid, or an aromatic or aliphatic nitrile compound.

11 Claims, No Drawings

HYDROXYLATION OF AROMATIC COMPOUNDS

This invention relates to a process for the nuclear hydroxylation of aromatic compounds. More particularly, this invention relates to a process for the nuclear hydroxylation of aromatic compounds having the formula $R_mArX_nH$ in which Ar is a monocyclic or polycyclic hydrocarbon nucleus, R is selected from the group consisting of carboxylic, sulfonic or phosphonic acid radicals, the alkali metal salts or alkaline earth metal salts of the acid radical, X is independently selected from the group consisting of hydrogen, alkyl, aryl, cycloalkyl, alkoxy, halogen and amino substituents, $m$ being an integer from 1 to about 5 and $n$ being an integer between 0 and 5, the sum of $m$ and $n$ being 5, which comprises treatment of said aromatic compounds with hydrogen peroxide in the presence of a catalyst comprising an alkaline solution containing a salt of hydrocyanic acid or an aromatic or aliphatic organic nitrile compound.

Hydroxylated aromatic acids are finding a wide variety of uses in the chemical field. For example, α-resorcylic acid which is also known as 3,5-dihydroxybenzoic acid is used as an intermediate for dyes, pharmaceuticals, light stabilizers and resins; β-resorcylic acid which is also known as 2,4-dihydroxybenzoic acid is also used as a dye stuff, as an intermediate in the preparation of pharmaceuticals or in the synthesis of organic chemicals. A third isomer of the dihydroxybenzoic acid which is gentisic acid also known as 2,5-dihydroxybenzoic acid is used in medicine as sodium gentisate. Another hydroxylated aromatic compound is gallic acid also known as 3,4,5-trihydroxybenzoic acid which is used for a variety of purposes including its use in photography, writing inks, dying, in the manufacturing of pyrogallol which itself has many uses, as a tanning agent and in the manufacture of tannins, in the manufacture of paper; in synthesis of pharmaceuticals, in process engraving, and lithography, etc. The hydroxylated benzene sulfonic acids and phosphonic acids may also be utilized in the synthesis of pharmaceuticals, paper manufacturing, as tanning agents and in process engraving. The hydroxylated aromatic acid disalts will have similar utility as hereinbefore set forth for the hydroxylated aromatic acids.

It is therefore an object of this invention to provide a process for hydroxylating aromatic acids or their alkali or alkaline earth metal salts.

A further object of this invention is to provide a process for introducing hydroxy substituents on the nucleus of the various aromatic acids or their alkali or alkaline earth metal salts to provide a useful chemical compound.

In one aspect an embodiment of this invention resides in a process for the nuclear hydroxylation of an aromatic compound having the formula $R_mArX_n$ in which Ar is a monocyclic or polycyclic hydrocarbon nucleus, R is selected from the group consisting of carboxylic, sulfonic or phosphonic acid radicals, the alkali metal salt or alkaline earth metal salts of the acid radicals, X is independently selected from the group consisting of hydrogen, alkyl, aryl, cycloalkyl, alkoxy, aralkyl, alkaryl, halogen and amino substituents, $m$ being an integer from 1 to about 5 and $n$ being an integer between 0 and 5 which comprises treating said aromatic compound with hydrogen peroxide at hydroxylation conditions in the presence of a catalyst comprising an alkaline solution containing a salt of hydrocyanic acid, or an aromatic or aliphatic organic nitrile, and recovering the resultant hydroxylated aromatic compound.

A specific embodiment of this invention resides in a process for preparing 2-hydroxybenzoic acid which comprises treating benzoic acid with hydrogen peroxide at a temperature of 50°C and a pressure of 1 atmosphere in the presence of a catalyst comprising benzonitrile in a sodium hydroxide solution, and recovering the resultant hydroxylated aromatic compound, namely 2-hydroxybenzoic acid.

Another specific embodiment of this invention resides in a process for preparing 2-hydroxybenzene sulfonic acid disodium salt which comprises treating sodium benzene sulfonate, at a temperature of 75°C and atmospheric pressure with hydrogen peroxide in the presence of a catalyst comprising butyronitrile in solution with potassium hydroxide and recovering the resultant hydroxylated aromatic compound, namely 2-hydroxybenzene sulfonic acid disodium salt.

Other objects and embodiments will be found in the following further detailed description of the present invention.

As hereinbefore set forth the present invention is concerned with the process for preparing hydroxylated aromatic compounds, said process being effected by treating an aromatic compound with hydrogen peroxide in the presence of a catalyst comprising an alkaline solution containing a salt of hydrocyanic acid, or an aromatic or aliphatic organic nitrile compound. The reaction is effected under conditions which include temperature in the range of from about −10°C to about 150°C and preferably from about 0°C to about 100° C. In addition, another reaction condition involves pressure, said pressure ranging from about atmospheric up to 100 atmospheric or more. When superatmospheric pressures are employed, said pressure is afforded by the introduction of a substantially inert gas such as nitrogen or helium into the reaction zone. Another variable which may be employed in the present invention is the amount of reactants, the hydrogen peroxide usually being present in a mol ratio in the range of from about 1:1 up to 1:10 mols of the hydrogen peroxide per mol of the aromatic compound.

Aromatic compounds which comprise the starting material for the process of this invention possess the generic Formula I:

$$R_mArX_nH$$

FORMULA I 

in which Ar is a monocyclic or polycyclic hydrocarbon nucleus, R is selected from the group consisting of carboxylic, sulfonic, or phosphonic acid radicals, the alkali metal salt or alkaline earth metal salts of the acid radicals, X is independently selected from the group consisting of hydrogen, alkyl, aryl, cycloalkyl, alkoxy, aralkyl, alkaryl, halogen and amino substituents, $m$ being an integer of from 1 to about 5 and n being an integer between 0 and 5, the total of $m$ and $n$ equaling 5. Some specific examples of these aromatic compounds which undergo nuclear hydroxylation will include benzoic acid, benzenesulfonic acid, benzenephosphonic acid, p-toluic acid, o-toluic acid, m-toluic acid, o-methylbenzenesulfonic acid, p-methylbenzenephosphonic acid, o-ethylbenzenesulfonic acid, m-ethylbenzoic acid, p-ethylbenzenephosphonic acid, o-propylbenzoic acid, m-propylbenzenesulfonic acid, p-propylbenzenephosphonic acid, o-isopropylbenzoic acid, m-isopropylbenzenesulfonic acid, p-isopropylbenzenephosphonic acid, o-n-butylbenzoic acid, m-n-butylbenzenesulfonic acid, p-n-butylbenzenephosphonic acid, 2,4-dimethylbenzoic acid, 2,5-dimethylbenzenesulfonic acid, 2,6-dimethylbenzenephosphonic acid, 2,4-ethylbenzoic acid, 2,5-diethylbenzenesulfonic acid, 2,6-diethylbenzenephosphonic acid, 2,4-dipropylbenzenesulfonic acid, 2,5-dipropylbenzenesulfonic acid, 2,6-dipropylbenzenesulfonic acid, 2,4-diisopropylbenzenephosphonic acid, 2,5-diisopropylbenzenephosphonic acid, 2,6-diisopropylbenzoic acid, 2,4,6-trimethylbenzoic acid, o-cyclohexylbenzoic acid, m-cyclohexylbenzenesulfonic acid, p-cyclohexylbenzenephosphonic acid, o-phenylbenzoic acid, m-phenylbenzenesulfonic acid, p-phenylbenzenephosphonic acid, o-benzylbenzoic acid, o-[4-tolyl]benzoic acid, m-[4-tolyl]benzenesulfonic acid, p-[4-tolyl]-benzenephosphonic acid, o-methoxybenzoic acid, m-methoxybenzenesulfonic acid, p-methoxybenzenephosphonic acid, o-ethoxybenzoic acid, m-ethoxybenzenesulfonic acid, p-ethoxybenzenephosphonic acid, 2,3,4,5-tetramethylbenzenesulfonic acid, 2,3,4,6-tetraethylbenzenephosphonic acid, 2-chlorobenzoic acid, 2-chlorobenzenesulfonic acid, 2-chlorobenzenephosphonic acid, 2,3-dichlorobenzoic acid, 2,3-dichlorobenzenesulfonic acid, 2,3-dichlorobenzenephosphonic acid, 2,3,4-trichlorobenzoic acid, 2,3,4-trichlorobenzenesulfonic acid, 2,3,4-trichlorobenzenephosphonic acid, 2-bromobenzoic acid, 2-bromobenzenesulfonic acid, 2-bromobenzenephosphonic acid, 2,3-dibromobenzoic acid, 2,3,4-tribromobenzenephosphonic acid, 2,3,4,5-tetrachlorobenzoic acid, 2,3,4,5-tetrabromobenzenesulfonic acid, 2,3,4,5-tetrabromobenzenephosphonic acid, 2-aminobenzenesulfonic acid, 2-aminobenzenephosphonic acid, 2-aminobenzoic acid, 2,3-diaminobenzoic acid, 2,3-diaminobenzenephosphonic acid, 2,3-diaminobenzenesulfonic acid, 2,3,4-triaminobenzoic acid, 2,3,4-triaminobenzenesulfonic acid, 2,3,4-triaminobenzenephosphonic acid, 2,3,4,5-tetraaminobenzenesulfonic acid, naphthoic acid, α-anthranoic acid, β-phenanthanoic acid, α-pyric acid, α-naphthalenesulfonic acid, β-naphthalenephosphonic acid, etc. It is also contemplated within the scope of this invention that the starting material may also comprise the alkali metal salt or alkaline earth metal salts of the various carboxylic, sulfonic and phosphonic acids. Suitable examples of these salts would include sodium benzoate, sodium benzenesulfonate, sodium benzenephosphonate, lithium benzoate, lithium benzenesulfonate, lithium benzenephosphonate, potassium benzoate, potassium benzenesulfonate, potassium benzenephosphonate, rubidium benzoate, rubidium benzenesulfonate, rubidium benzenephosphonate, cesium benzoate, cesium benzenesulfonate, cesium benzenephosphonate, magnesium benzoate, magnesium benzenesulfonate, magnesium benzenephosphonate, calcium benzoate, calcium benzenesulfonate, calcium benzenephosphonate, strontium benzoate, strontium benzenesulfonate, strontium benzenephosphonate, barium benzoate, barium benzenesulfonate, barium benzenephosphonate, sodium terephthalate, calcium phthalate, calcium isophthalate, 2-methyl sodium benzoate, calcium benzenesulfonate, magnesium 3-methylbenzenephosphonate, cesium benzenesulfonate, rubidium 3-chlorobenzenephosphonate, sodium 2,3-dichlorobenzoate, rubidium 2-aminobenzenephosphonate, 2,4-diaminobenzenephosphonate, etc.

It is contemplated within the scope of this invention that the aromatic compound may be treated with hydrogen peroxide (common name of $H_2O_2$) at hydroxylation conditions in the presence of a catalyst comprising an alkaline solution containing a salt of hydrocyanic acid, or an aromatic or aliphatic organic nitrile compound. The term alkaline solution as used in the specification and the appended claims is defined to mean a solution in which there remains free base such as sodium hydroxide or potassium hydroxide present after any free carboxylic, sulfonic or phosphonic acid groups are neutralized plus an equivalent amount of base for each mole of hydrogen peroxide charged. As hereinbefore set forth the alkaline solution contains a salt of hydrocyanic acid, or an aromatic or aliphatic organic nitrile compound. Suitable examples of salts of hydrocyanic acid would include sodium cyanide, calcium cyanide, magnesium cyanide, rubidium cyanide, etc. Suitable examples of aromatic or aliphatic organic nitriles would include benzonitrile, o-methylbenzonitrile, m-methylbenzonitrile, p-methylbenzonitrile, o-ethylbenzonitrile, m-ethylbenzonitrile, p-ethylbenzonitrile, etc.; acetonitrile, propionitrile, butyronitrile, pentanonitrile, capronitrile, heptanonitrile, caprylnitrile, etc. The alkaline solution of the catalyst of the present invention may be afforded by the presence of any relatively strong base such as sodium hydroxide, potassium hydroxide, calcium hydroxide, lithium hydroxide, magnesium hydroxide, etc. It is understood that the aforementioned aromatic compounds and catalysts comprising an alkaline solution containing a salt of hydrocyanic acid or an aromatic or aliphatic organic nitrile compound are only representative of the class of compounds which may be used and that the present invention is not necessarily limited thereto.

The process of the present invention may be effected in either a batch or continuous type operation. For example, when a batch type operation is used, a quantity of the aromatic acid or acid salt is placed in an appropriate apparatus such as, for example, a stirred autoclave along with a catalyst comprising an alkaline solution containing a salt of a hydrocyanic acid, or an aromatic or aliphatic organic nitrile compound. The hydrogen peroxide is added thereto and the reaction allowed to proceed for a predetermined residence time under the hydroxylation conditions hereinbefore set forth in greater detail. The residence time may vary from about 0.5 hour up to about 5 hours or more in duration. Upon completion of the desired residence time the reaction product is recovered. Following this, the reaction product is subjected to conventional means for recovery, said means including washing the product with an inert organic solvent, flashing off the solvent and subjecting the reaction product to fractional distillation or crystallization to recover the desired compounds.

It is also contemplated that the process of this invention may be effected in a continuous manner of operation. When such a process is used the aromatic compound which is to undergo hydroxylation and the catalyst comprising an alkaline solution containing a salt of hydrocyanic acid, or an aromatic or aliphatic organic nitrile compound are continuously charged to a reaction zone in which proper operating conditions of temperature and pressure are maintained. The alkalinity of the solution is maintained or modified by an on-stream pH meter. In addition, the hydrogen peroxide in the form of an aqueous solution containing from about 5% to about 90% or more of hydrogen peroxide is continuously charged to the reaction zone in slow and deliberate manner. The reaction is allowed to proceed for a predetermined residence time, following which the reactor effluent is continuously withdrawn. The reaction product in the reactor effluent is separated from the unreacted aromatic compound by conventional means of the type hereinbefore set forth and passed to storage while any unreacted aromatic compound or catalyst comprising an alkaline solution containing a salt of hydrocyanic acid, or an aromatic or aliphatic organic nitrile may be recycled to form a portion of the feedstock.

Examples of hydroxylated aromatic compounds which may be prepared according to the process of this invention include 5-hydroxy-o-toluic acid, 3,4-hydroxy-o-toluic acid, 5-hydroxy-m-toluic acid, 5-hydroxy-p-toluic acid, 3,5-dihydroxy-p-toluic acid, 5-hydroxy-2-ethylbenzoic acid, 5-hydroxy-3-ethylbenzenesulfonic acid, 5-hydroxy-3-ethylbenzenephosphonic acid, 3-hydroxy-4-ethylbenzoic acid, 3,4-dihydroxy-4-ethylbenzenesulfonic acid, 5-hydroxy-2-propylbenzenephosphonic acid, 5-hydroxy-3-propylbenzoic acid, 3-hydroxy-4-propylbenzenesulfonic acid, 3,5-dihydroxy-4-propylbenzenephosphonic acid, 5-hydroxy-2-isopropylbenzoic acid, 5-hydroxy-3-isopropylbenzenesulfonic acid, 3-hydroxy-4-isopropylbenzenephosphonic acid, 3,5-dihydroxy-4-isopropylbenzoic acid, 5-hydroxy-o-n-butylbenzenesulfonic acid, 5-hydroxy-3-n-butylbenzenephosphonic acid, 3-hydroxy-4-t-butylbenzoic acid, 3,5-dihydroxy-4-n-butylbenzenesulfonic acid, 3-hydroxy-4-n-butylbenzenephosphonic acid, 3,5-dihydroxy-4-n-butylbenzoic acid, 3-hydroxy-2,4-dimethylbenzenesulfonic acid, 3-hydroxy-2,5-dimethylbenzenephosphonic acid, 5-hydroxy-2,6-dimethylbenzoic acid, 5-hydroxy-2,4,6-trimethylbenzenesulfonic acid, 3,5-dihydroxy-2,4,6-trimethylbenzenephosphonic acid, 5-hydroxy-2-cyclohexylbenzoic acid, 5-hydroxy-2-phenylbenzenesulfonic acid, 3,5-dihydroxy-4-phenylbenzenephosphonic acid, 2,3-dihydroxybenzoic acid, 3,4-dihydroxybenzenesulfonic acid, 2,5-dihydroxybenzenephosphonic acid, 3,4,5-trihydroxybenzoic acid, 2,3-dihydroxy-4-methylbenzenesulfonic acid, 2,5-dihydroxy-4-methylbenzenephosphonic acid, 5-hydroxy-2-methoxybenzenephosphonic acid, 5-hydroxy-2-methoxybenzoic acid, 3,5-dihydroxy-4-methoxybenzenesulfonic acid, 5-hydroxy-2-ethoxybenzenephosphonic acid, 3-hydroxy-4-ethoxybenzoic acid, 3,5-dihydroxy-4-ethoxybenzenesulfonic acid, 4-hydroxy-1-methyl-2-naphthoic acid, 3,4-dihydroxy-1-methyl-2-naphthoic acid, 1,4-dihydroxy-2-naphthoic acid, 3,4-dihydroxy-1-naphthoic acid. It is also contemplated within the hydroxylation of the aromatic compound that a dialkali or dialkaline salt of the precursor aromatic acid may be formed. Examples of such disalts would include 2-hydroxybenzenesulfonic acid disodium salt, 3-hydroxybenzoic acid dipotassium salt, 4-hydroxybenzenephosphonic acid dirubidium salt, etc. It is to be understood that the aforementioned hydroxylated aromatic compounds are only representative of the class of compounds which may be prepared, and that the process of the present invention as described herein is not necessarily limited thereto.

The following examples are given to illustrate the process of the present invention which, however, are not intended to limit the generally broad scope of the present invention in strict accordance therewith.

EXAMPLE I

In this example 122.0 grams (1.0 moles) of benzoic acid are placed in a stainless steel autoclave containing 15.0 grams of benzonitrile and 500 grams of water containing 200.0 grams (5.0 moles) of sodium hydroxide. Thereafter, 12.0 grams of a 30 percent aqueous hydrogen peroxide solution is added to the autoclave during a period of time comprising 22 minutes. The autoclave is maintained at a temperature of 50°C and a pressure of one atmosphere during the entire 22 minutes of treatment time. At the end of the 22 minutes, the autoclave is allowed to return to room temperature and the treatment product transferred to a clean dry beaker. The treatment product is acidified, extracted with ether and the ether layer evaporated to produce a crude product. Fractional crystallization of the crude product in water and alcohol yields essentially pure 2-hydroxybenzoic acid, 3-hydroxybenzoic acid and 4-hydroxybenzoic acid.

EXAMPLE II

In this example 164.0 grams (1.0 moles) of sodium benzenesulfonate, the alkali metal salt of benzenesulfonic acid, are placed in a stainless steel turbomixer autoclave containing 71.0 grams butyronitrile and 400.0 grams of water containing 60.0 grams (1.5 moles) of sodium hydroxide. Thereafter, 24.0 grams of a 90 percent aqueous hydrogen peroxide solution is added to the autoclave during a period of time comprising 50 minutes. During this time, the autoclave is maintained at a temperature of 50°C and a pressure of 5 atmospheres afforded by the introduction of substantially inert nitrogen gas. At the end of the 50 minutes, the heat is terminated and the autoclave is vented thereby allowing it to return to ambient pressure and room temperature. The treatment product is transferred to a clean, dry beaker, neutralized with sulfonic acid and extracted by an ether wash. The ether is removed from the treatment product by evaporation on a steam bath, thereby producing a crude reaction product. The treatment product is subjected to analysis by means of nuclear magnetic resonance spectroscopy instrumentation, said analysis disclosing the product to contain 2-hydroxybenzenesulfonic acid, 3-hydroxybenzenesulfonic acid, 4-hydroxybenzenesulfonic acid and 2-hydroxybenzenesulfonic acid disodium salts.

EXAMPLE III

In this example 158.0 grams (1.0 mole) of benzenephosphonic acid are placed in a stainless steel autoclave containing 19.0 grams of propionitrile dissolved in water containing 116.0 grams (2.0 moles) of potassium hydroxide. Thereafter, 30.0 grams of a 50% aqueous hydrogen peroxide is added to the autoclave during a period of time comprising 60 minutes. The autoclave is maintained at a temperature of 0°C by means of an ice bath and a pressure of 10 atmospheres afforded by the introduction of substantially inert nitrogen gas. At the end of the 60 minutes, the ice bath is removed and the autoclave is vented thereby allowing it to return to ambient pressure and room temperature. The treatment product is transferred to a beaker, neutralized, and extracted by an ether wash. The ether is removed from the treatment product by evaporation, thereby producing a crude product. The product is subjected to analysis by means of nuclear magnetic spectroscopy instrumentation, said analysis disclosing the product to contain 2-hydroxybenzenephosphonic acid.

EXAMPLE IV

In this example 157.0 grams (1.0 mole) of 2-chlorobenzoic acid are placed in a stainless steel autoclave containing 32.0 grams of potassium cyanide, a salt of hydrocyanic acid, 500.0 grams of water, and 48.0 grams (2.0 moles) of lithium hydroxide. Thereafter, 20.0 grams of hydrogen peroxide is added to the autoclave during a period of time comprising 90 minutes. The autoclave is maintained at a temperature of 100°C and a pressure of 25 atmospheres afforded by the introduction of substantially inert helium gas. At the end of the 90 minutes, the heat is terminated and the autoclave is vented thereby allowing it to return to ambient pressure and room temperature. The treatment product is transferred to an apparatus for neutralization, said apparatus being equipped to trap the lethal hydrogen cyanide as the iron complex. The acidified mixture is extracted by an ether wash, and the ether is removed from the product by use of a film evaporation, thereby yielding a crude product. The product is subjected to analysis by means of nuclear magnetic resonance spectroscopy instrumentation, said analysis disclosing the product to comprise polyhydroxy-substituted isomers of 2-chlorobenzoic acid.

I claim as my invention:

1. A process for the nuclear hydroxylation of an aromatic compound having the formula $R_mArX_nH$ in which Ar is a monocyclic or polycyclic hydrocarbon nucleus, R is selected from the group consisting of carboxylic, sulfonic, phosphonic acid groups, alkali metal salt or alkaline earth metal salts of the acids, X is independently selected from the group consisting of hydrogen, alkyl, aryl, cycloalkyl, alkoxy, aralkyl, alkaryl, halogen and amino substituents, $m$ being an integer from 1 to about 5 and $n$ being an integer between 0 and 5, which comprises reacting said aromatic compound with hydrogen peroxide at a temperature of from about −10°C. to about 150°C., a pressure of from about atmospheric to about 100 atmospheres and a mol ratio of from about 1:1 to about 1:10 mols of hydrogen peroxide per mol of aromatic compound in the presence of a catalyst consisting essentially of an alkaline solution of an aromatic nitrile selected from the group consisting of benzonitrile and alkyl benzonitrile and recovering the resultant hydroxylated aromatic compound.

2. The process of claim 1 further characterized in that the aromatic nitrile is an alkyl benzonitrile.

3. The process of claim 1 further characterized in that the aromatic nitrile is benzonitrile.

4. The process of claim 1 further characterized in that the alkaline solution comprises aqueous sodium hydroxide.

5. The process of claim 1 further characterized in that the alkaline solution comprises aqueous potassium hydroxide.

6. The process of claim 1 further characterized in that the alkaline solution comprises aqueous lithium hydroxide.

7. The process of claim 1 further characterized in that the aromatic compound is benzoic acid and the resultant hydroxylated compound is 2-hydroxybenzoic acid.

8. The process of claim 1 further characterized in that the aromatic compound is sodiumbenzenesulfonate and the resultant hydroxylated compound is 2-hydroxybenzenesulfonic acid disodium salt.

9. The process of claim 1 further characterized in that the aromatic compound is benzenephosphonic acid and the resultant hydroxylated compound is 2-hydroxybenzenephosphonic acid.

10. The process of claim 1 further characterized in that the aromatic compound is 2-chlorobenzoic acid and the resultant hydroxylated compounds are polyhydroxy-substituted isomers of 2-chlorobenzoic acid.

11. The process of claim 1 further characterized in that the aromatic compound is 4-aminobenzenesulfonic acid and the resultant hydroxylated compounds are hydroxy-substituted isomers of 4-aminobenzenesulfonic acid.

* * * * *